United States Patent
Itoh

(10) Patent No.: US 7,504,067 B2
(45) Date of Patent: Mar. 17, 2009

(54) AUTOMATIC TUBE-TYPE SPECIMEN CONTAINER SUPPLY APPARATUS

(76) Inventor: Teruaki Itoh, 5-25, Kokaihommachi, Kumamoto-shi, Kumamoto-ken (JP)

( * ) Notice: Subject to any disclaimer, the term of this patent is extended or adjusted under 35 U.S.C. 154(b) by 696 days.

(21) Appl. No.: 10/724,709

(22) Filed: Dec. 2, 2003

(65) Prior Publication Data

US 2004/0109791 A1    Jun. 10, 2004

(30) Foreign Application Priority Data

Dec. 2, 2002    (JP)    ............................ 2002-349951

(51) Int. Cl.
*G01N 31/00*    (2006.01)
*B65H 3/32*    (2006.01)

(52) U.S. Cl. .............................. 422/63; 422/65; 422/99; 156/538; 156/556; 156/566; 221/258; 221/224; 221/254

(58) Field of Classification Search .................. 422/63, 422/65, 99; 436/44; 221/157, 163, 171, 221/258, 224, 254; 156/538, 556, 566
See application file for complete search history.

(56) References Cited

U.S. PATENT DOCUMENTS

| | | | | |
|---|---|---|---|---|
| 488,084 | A | * | 12/1892 | Miner .......................... 221/238 |
| 3,777,932 | A | * | 12/1973 | Matsui et al. ................. 221/204 |
| 4,567,997 | A | * | 2/1986 | Portyansky ................... 221/233 |
| 5,097,938 | A | * | 3/1992 | Gruner et al. ............. 198/397.04 |
| 5,893,263 | A | * | 4/1999 | Matsumoto et al. .......... 156/387 |
| 6,039,209 | A | * | 3/2000 | Yuyama et al. .............. 221/171 |
| 6,138,868 | A | * | 10/2000 | Yuyama et al. .......... 221/312 R |
| 6,189,728 | B1 | * | 2/2001 | Yuyama et al. ................ 221/17 |
| 6,325,129 | B1 | * | 12/2001 | Wright et al. ................ 156/538 |
| 6,505,756 | B1 | * | 1/2003 | Walldorf et al. ............. 221/241 |
| 7,299,943 | B2 | * | 11/2007 | Itoh ......................... 221/312 R |
| 2004/0031809 | A1 | * | 2/2004 | Itoh ........................... 221/208 |
| 2004/0108330 | A1 | * | 6/2004 | Itoh ........................... 221/289 |

FOREIGN PATENT DOCUMENTS

| | | |
|---|---|---|
| JP | 7-35437 | 7/1995 |
| JP | 7-213586 | 8/1995 |
| JP | 2002-306952 | 10/2002 |

* cited by examiner

*Primary Examiner*—Jill Warden
*Assistant Examiner*—P. Kathryn Wright
(74) *Attorney, Agent, or Firm*—Nixon & Vanderhye P.C.

(57) ABSTRACT

An automatic tube-type specimen container supply apparatus includes a container storing box a bottom of which has a tapered surface having a container collecting position in a lowest part thereof to collect a plurality of tube-type specimen containers in one spot, a container individually-sending mechanism which lifts up the collected specimen containers one by one along one-side wall located close to the position, an outlet which allows the specimen containers to be discharged outside the box, and a container carry-out mechanism including a conveyor to automatically carry out the discharged specimen containers. The container individually-sending mechanism includes a lifting plate driven up and down and having a top end with a tapered surface. The tapered surface has a space to place only one specimen container lying on a side thereof and descending toward an outside of the container storing box.

2 Claims, 3 Drawing Sheets

AUTOMATIC TUBE-TYPE SPECIMEN CONTAINER SUPPLY APPARATUS

CROSS-REFERENCE TO RELATED APPLICATIONS

This application is based upon and claims the benefit of priority from the prior Japanese Patent Application No. 2002-349951, filed Dec. 2, 2002, the entire contents of which are incorporated herein by reference.

BACKGROUND OF THE INVENTION

1. Field of the Invention

The present invention relates to an automatic tube-type specimen container supply apparatus for automatically supplying tube-type specimen containers that are used to dispense a large number of specimens such as blood and urine.

2. Description of the Related Art

In order to dispense a large number of specimens such as blood and urine, a large number of tube-type specimen containers are required as slave specimen containers. If a user purchases tube-type specimen containers that are held in a rack, his or her running costs will increase. If a user purchases tube-type specimen containers that are not held in a rack, he or she needs to expend much effort to hold the specimen containers in a rack though the unit price of the specimen containers reduces. As one measure against this, a specimen container supply apparatus using a parts feeder has been in practical use. However, this apparatus is so noisy that it makes work environment much worse.

Jpn. Pat. Appln. KOKAI Publication No. 07-213586 discloses an automatic specimen container supply apparatus. This apparatus is capable of removing specimen containers (test tubes), which are arranged in a hopper, one by one using a rotary drum. The rotary drum is located at the bottom of the hopper and is provided with a groove for removing the specimen containers.

The apparatus disclosed in the above Publication is a breakthrough in that it can remove specimen containers one by one. However, the apparatus cannot remove any specimen containers that are randomly inserted in the hopper. The specimen containers are removed downward through an outlet formed in the lower part of the hopper by the rotary drum. If, therefore, a large number of specimen containers concentrate in the outlet, the outlet is likely to be clogged by the weight of the specimen containers themselves.

BRIEF SUMMARY OF THE INVENTION

An object of the present invention is to provide an automatic tube-type specimen container supply apparatus having the following advantages.

1) The randomly inserted specimen containers can be removed one by one and supplied to a position for use.

2) There is no fear that the outlet will be clogged with the specimen containers.

In order to attain the above object, an automatic tube-type specimen container supply apparatus according to the present invention has the following characteristic configuration. The other characteristic configurations will be clarified in the embodiment.

An automatic tube-type specimen container supply apparatus according to an embodiment of the present invention, comprises a container storing box a bottom of which has a tapered surface having a container collecting position in a lowest part thereof to collect a plurality of tube-type specimen containers in one spot through an insertion port, a container individually-sending mechanism configured to lift up the specimen containers, which are collected in the container collecting position, one by one along one side wall located close to the container collecting position, an outlet formed in the one side wall to discharge the specimen containers, which are lifted up by the container individually-sending mechanism, outside the container storing box, and a container carry-out mechanism including a carry-out conveyor to automatically carry out the specimen containers discharged through the outlet, wherein the container individually-sending mechanism includes a drive source and a lifting plate which is driven up and down by the drive source, and the lifting plate has a top end with a tapered surface, the tapered surface having a space to place only one specimen container lying on a side thereof and descending toward an outside of the container storing box.

DETAILED DESCRIPTION OF THE INVENTION

Embodiment

Figure 1:
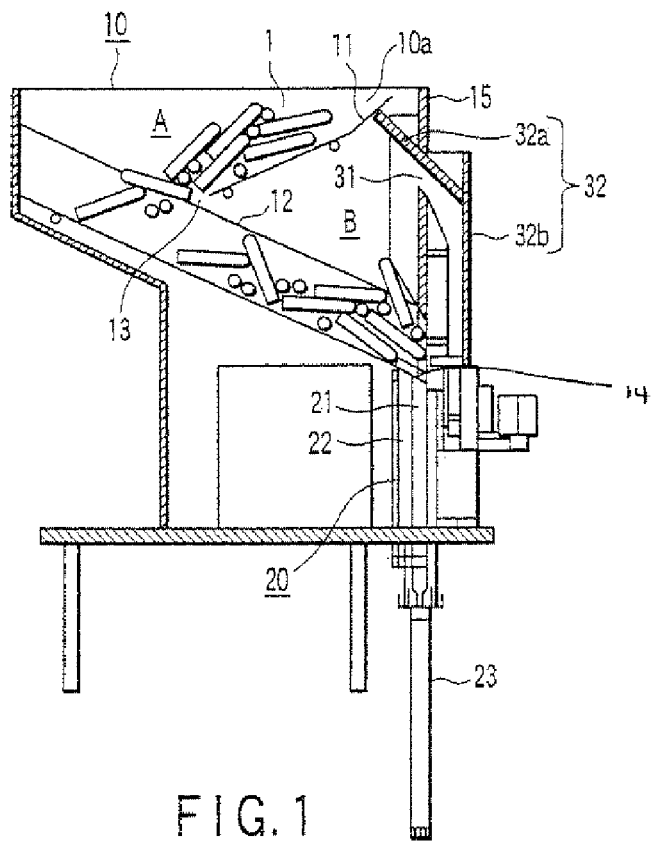
FIG. 1 is a schematic sectional view of the side of the container-storing box (when a lifting plate is lowered), illustrating the entire configuration and operation of the automatic tube-type specimen container supply apparatus according to the embodiment of the present invention.
Figure 2:
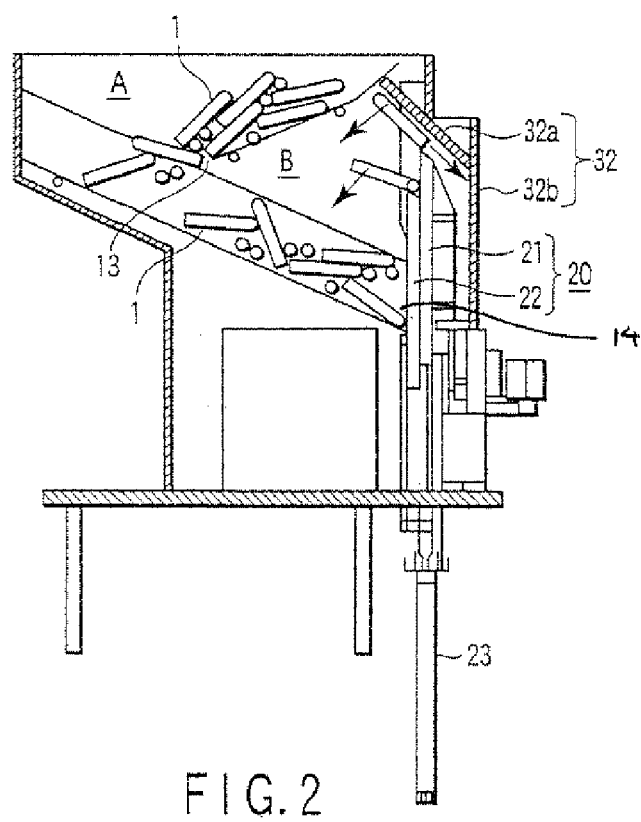
FIG. 2 is a schematic sectional view of the side of the container-storing box (when the lifting plate is raised), illustrating the entire configuration and operation of the automatic tube-type specimen container supply apparatus according to the embodiment of the present invention.

FIGS. 1 and 2 illustrate a container storing box 10 having an insertion port 10a on its top end. The bottom of the box 10 has a tapered surface in order to collect a plurality of resin or glass-made tube-type specimen containers 1 that are randomly inserted through the insertion port 10a. A container collecting position 14 is located in the lowermost part of the tapered surface.

The bottom of the box 10 has a two-layer structure including a first partition plate 11 and a second partition plate 12 that are vertically opposed to each other. The first partition plate 11 has a tapered surface that descends gently from one side to the other side. The second partition plate 12 has a tapered surface that descends gently in the direction opposite to the tapered surface of the first partition plate 11. The upper layer of the box 10 is formed of room A and the lower layer thereof is formed of room B. A relatively narrow path 13 is formed between the first and second partition plates 11 and 12 to allow the specimen containers to pass therethrough one by one while lying on their sides.

A container individually-sending mechanism 20 is so provided that it can push up specimen containers 1, which are collected in the container collecting position 14, one by one along one side wall 15 located close to the position 14.

Figure 3:
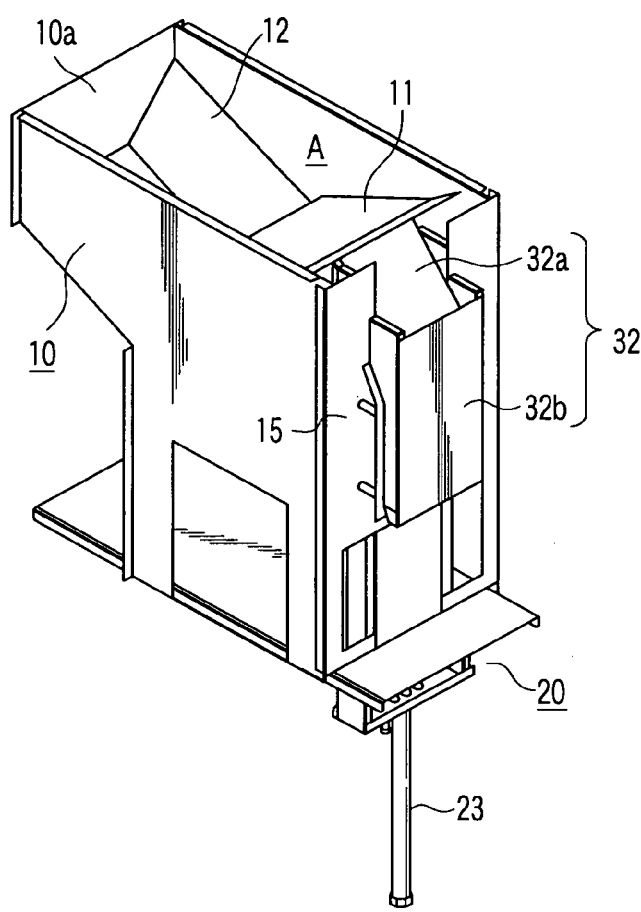
FIG. 3 is a perspective view showing an outward appearance of the automatic tube-type specimen container supply apparatus according to the embodiment of the present invention.
Figure 4:
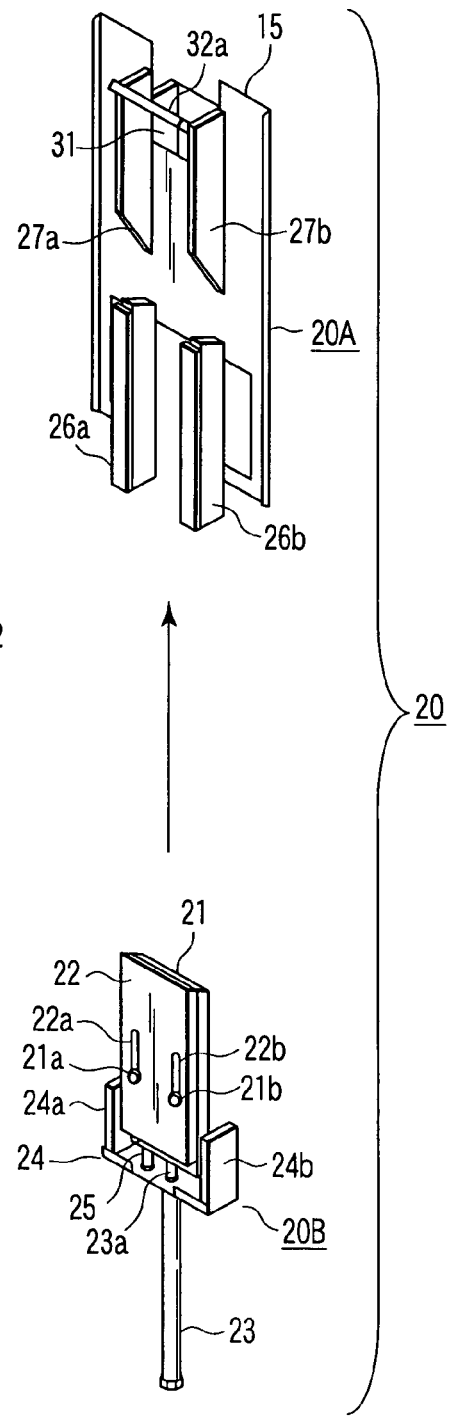
FIG. 4 is an exploded perspective view of a movable section of the automatic tube-type specimen container supply apparatus according to the embodiment of the present invention.

Referring to FIGS. 3 and 4, the container individually-sending mechanism 20 includes a fixing section 20A and a movable section 20B. The fixing section 20A has a pair of plate guide blocks 26a and 26b and a pair of plate guide walls 27a and 27b on the inner surface of the sidewall 15. The plate guide blocks 26a and 26b are arranged in parallel at a fixed interval therebetween, as are the plate guide walls 27a and 27b. The sidewall 15 has an outlet 31 (described later) on its top. A guide plate 32a (described later) is attached to a region above the outlet 31.

The movable section 20B includes a U-shaped mounting base 24. The mounting base 24 has a pair of mounting pieces 24a and 24b at both ends. The mounting pieces 24a and 24b are combined with their respective plate guide blocks 26a and 26b of the fixing section 20A. Thus, the fixing section 20A and movable section 20B are formed integrally as one component.

A drive source 23, which is formed of, e.g., an air piston device, is mounted on the underside of the mounting base 24. A drive shaft 23a of the drive source, which penetrates the mounting base 24, is coupled to the bottom end of a lifting plate 21. Thus, the lifting plate 21 can be reciprocated up and down by the drive source 23.

Figure 5A:
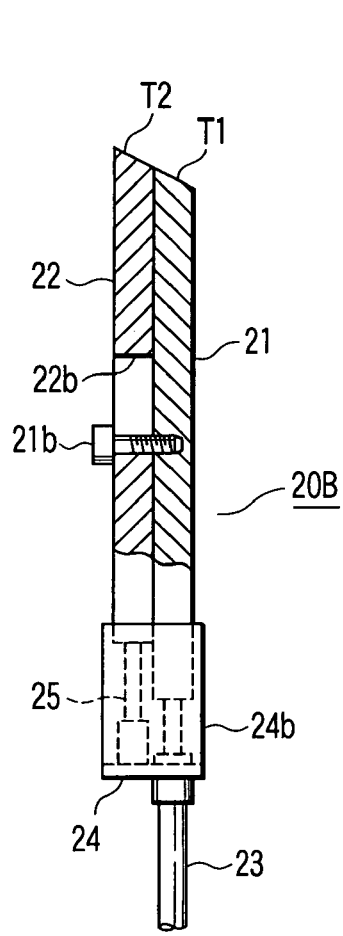
FIG. 5A is a partly cutaway side view of a movable section of a container individually-sending mechanism (when the lifting plate is lowered) of the automatic tube-type specimen container supply apparatus according to the embodiment of the present invention.
Figure 5B:
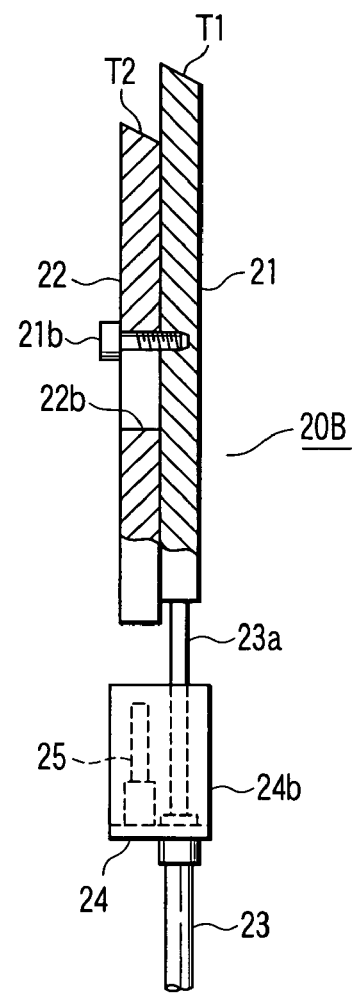
FIG. 5B is a partly cutaway side view of a movable section of a container individually-sending mechanism (when the lifting plate is raised) of the automatic tube-type specimen container supply apparatus according to the embodiment of the present invention.

The lifting plate 21 is formed of a plate-like element and its top end has a tapered surface T1 as illustrated in FIGS. 5A and 5B. The tapered surface T1 has a long, narrow space in which only one specimen container 1 can be placed lying on its side. The tapered surface T1 descends toward the outside of the container storing box 10.

An auxiliary plate 22 is mounted on one side (left side in FIGS. 5A and 5B) of the lifting plate 21. The auxiliary plate 22 can slide up and down relative to the lifting plate 21. More specifically, pins 21a and 21b are implanted into the lifting plate 21 and long slits 22a and 22b are formed in the auxiliary plate 22. The pins 21a and 21b are fitted into the slits 22a and 22b, respectively. Like the top end of the lifting plate 21, the top end of the auxiliary plate 22 has a tapered surface T2 that descends toward the outside of the container storing box 10. When the auxiliary plate 22 descends to a given level, its bottom end contacts a stopper 25 on the mounting base 24, with the result that the auxiliary plate 22 is prevented from descending beyond the level.

When the lifting plate 21 descends, the top end of the lifting plate 21 and that of the auxiliary plate 22 are flush with each other (the tapered surfaces T1 and T2 are flush with each other) as shown in FIG. 5A. When the lifting plate 21 ascends, the top end of the auxiliary plate 22 is located at a lower level than that of the lifting plate 21 as shown in FIG. 5B.

Referring back to FIGS. 1 and 2, a container carry-out mechanism has an outlet 31 on its one sidewall 15, as described above. The outlet 31 is used to discharge the specimen containers 1, which are lifted up by the container individually-sending mechanism 20, outside the container-storing box 10. A specimen container-discharging guide section 32 is coupled to the outlet 31. The guide section 32 includes a guide plate 32a provided at a section coupled to the outlet 31 and a guide path 32b that communicates with the guide plate 32a and guides the specimen containers 1 to a carry-out conveyor. The carry-out conveyor is made of, e.g., rubber and automatically carries the specimen containers 1 outside the box from the guide section 32.

An operation of the automatic tube-type specimen container supply apparatus so configured will now be described. Tube-type specimen containers (e.g., slave specimen containers) 1 to be supplied automatically are randomly inserted into the room A through the insertion port 10a by hand. Some of the inserted specimen containers 1 enter the room B from the room A through the path 13 formed in the boundary between the rooms A and B. Then, the specimen containers are collected in the container collecting position 14 that is the lowest position of the container storing box 10. Of the specimen containers 1 collected in the position 14, the specimen containers placed on the tapered surface T1 of the top end of the lifting plate 21 of the mechanism 20 are lifted up to the level of the outlet 31 as the plate 21 rises.

When a specimen container 1 is lifted up in an upright position, its top end contacts the bottom end of the guide plate 32a that is inclined. The center of gravity of the specimen container 1 is therefore inclined toward the inside of the box 10. Consequently, the specimen container 1 drops again toward the bottom of the box 10. Only one specimen container 1 is placed on the top end of the lifting plate 21. Thus, only one specimen container 1, which is lifted up lying on its side, is discharged outside the box through the outlet 31. The discharged specimen container 1 reaches the carry-out conveyor through the guide path 32b. The specimen containers 1 that have reached the carry-out conveyor are automatically carried one by one outside the box 10 by the carry-out conveyor. The above carry-out operation is performed each time the lifting plate 21 moves up and down.

When the carry-out operation continues, the specimen containers 1 are moved away from the periphery of the lifting plate 21. Thus, the specimen containers 1 cannot be lifted up even though the lifting plate 21 repeats its lifting operation again and again.

The above drawback does not occur because the lifting plate 21 is provided with the auxiliary plate 22. More specifically, when the lifting plate 21 descends, the bottom end of the auxiliary plate 22 is supported by the top end of the stopper 25. The top end of the auxiliary plate 22 thus becomes flush with that of the lifting plate 21. The slave specimen container 1 slides on the above tapered surface and is smoothly placed on the top end of the lifting plate 21. When the lifting plate 21 ascends, the top end of the auxiliary plate 22 is located at a lower level than that of the lifting plate 21. In other words, the flush-surface state that is obtained when the lifting plate 21 descends is released to thereby form a step between the top ends of the lifting plate 21 and auxiliary plate 22. By performing this operation, the wall of a block of specimen containers 1 to be formed around the plates 21 and 22 is crumbled.

When the lifting plate 21 descends again, the specimen containers 1 smoothly slide on the tapered surface from the top end of the auxiliary plate 22 to that of the lifting plate 21. Thus, one or more specimen containers 1 are always placed on the lifting plate 21 that has descended. The operation for sending out the specimen containers 1 is performed without fail.

As a result of the repetition of the above operation, the foregoing drawback does not occur and the specimen containers are reliably lifted up whenever the lifting plate 21 ascends. In the above embodiment, an air piston cylinder device is used as the drive source 23; therefore, noise can be reduced to a minimum.

Features of the Embodiment

[1] An automatic tube-type specimen container supply apparatus according to an embodiment, comprises:

a container storing box 10 a bottom of which has a tapered surface having a container collecting position 14 in a lowest part thereof to collect a plurality of tube-type specimen containers 1 in one spot through an insertion port 10a;

a container individually-sending mechanism 20 configured to lift up the specimen containers 1, which are collected in the container collecting position 14, one by one along one side wall 15 located close to the container collecting position 14;

an outlet 31 formed in the one side wall 15 to discharge the specimen containers 1, which are lifted up by the container individually-sending mechanism 20, outside the container storing box 10; and a container carry-out mechanism including a carry-out conveyor to automatically carry out the specimen containers 1 discharged through the outlet 31, wherein the container individually-sending mechanism 20 includes a drive source 23 and a lifting plate 21 which is driven up and down by the drive source 23, and the lifting plate 21 has a top end with a tapered surface T1, the tapered surface T1 having a space to place only one specimen container lying on a side thereof and descending toward an outside of the container storing box 10.

In the automatic tube-type specimen container supply apparatus described above, whenever the lifting plate 21 ascends, only one specimen container 1 lying on its side on the top end of the plate 21 is discharged outside the box through the outlet 31. Consequently, the specimen containers 1 are automatically carried outside the box one by one and thus supplied to a given position. Since, moreover, the specimen containers lifted up from below the box by the lifting plate 21 are removed from the outlet 31 provided in the upper part of the box, there is no fear that the outlet 31 will be clogged.

[2] The automatic tube-type specimen container supply apparatus according to above item [1], further comprises an auxiliary plate 22 mounted on one side of the lifting plate 21 such that the auxiliary plate 22 is slidable up and down relative to the lifting plate 21, and the auxiliary plate 22 has a top end with a tapered surface T2 that descends toward an outside of the container storing box 10, the top end of the auxiliary plate 22 being flush with that of the lifting plate 21 when the lifting plate descends and being located in a lower level than that of the lifting plate 21 when the lifting plate 21 ascends.

In the automatic tube-type specimen container supply apparatus described above, whenever the lifting plate 21 moves up and down, the wall of a block of specimen containers to be formed around the lifting plate 21 is crumbled by the function of the auxiliary plate 22. Thus, the specimen containers are always placed on the lifting plate 21 that has descended. The operation for sending out the specimen containers 1 is performed without fail.

[3] In the automatic tube-type specimen container supply apparatus according to one of above items [1] and [2], the container storing box 10 has a two-layer structure including a first partition plate 11 and a second partition plate 12 that are vertically opposed to each other, the first partition plate 11 having a tapered surface that descends from one side to another side, the second partition plate 12 having a tapered surface that descends in a direction opposite to the tapered surface of the first partition plate 11, and a path 13 is formed between the first and second partition plates 11 and 12 to allow one specimen container to pass therethrough.

In the automatic tube-type specimen container supply apparatus described above, the inserted specimen containers 1 are supplied to the container collecting position 14 with limitations in number and position. Therefore, the specimen containers 1 can be prevented from being collected simultaneously in the container collecting position 14 to an excessive degree, and the lifting plate 21 can smoothly be moved up and down.

Modification

The automatic tube-type specimen container supply apparatus according to the embodiment of the present invention can be modified as follows.

A motor or a rotary solenoid can be used as the drive source 23.

What is claimed is:

1. An automatic tube-type specimen container supply apparatus comprising:

a container storing box having a plurality of side walls, an insertion port and a bottom, said bottom of said container storing box including a tapered surface having a container collecting position in a lowest part thereof to collect a plurality of tube-type specimen containers;

a container individually-sending mechanism configured to lift up said specimen containers, which are collected in said container collecting position, one by one along one of said side walls;

an outlet formed in the one of said side walls to discharge the specimen containers, which are lifted up by the container individually-sending mechanism, outside the container storing box; and a container carry-out mechanism including a carry-out conveyor to carry out the specimen containers discharged through the outlet, wherein the container individually-sending mechanism includes a single drive source for lifting up said specimen containers, a lifting plate which is driven up and down by the drive source, and an auxiliary plate which is mounted on one side of and adjacent the lifting plate, the lifting plate including a pin engageable with and displaceable in a slit in the auxiliary plate, the drive source driving only the lifting plate such that the auxiliary plate is slidable up and down in accordance with movement of the lifting plate only by engagement of the pin with the slit, the lifting plate has a top end with a tapered surface having a space to place only one specimen container and descending toward an outside of the container storing box, and the auxiliary plate has a top end with a tapered surface that descends toward an outside of the container storing box, the lifting plate and the pin and the auxiliary plate and the slit being constructed such that the top end of the auxiliary plate is flush with that of the lifting plate when the lifting plate descends and is located in a lower level than that of the lifting plate when the lifting plate ascends.

2. The automatic tube-type specimen container supply apparatus according to claim 1, wherein the container storing box has a two-layer structure including a first partition plate and a second partition plate that are angled downwardly with respect to a horizontal plane, the first partition plate having a tapered surface that descends from one side to another side, the second partition plate having a tapered surface that descends in a direction opposite to the tapered surface of the first partition plate, and a path is formed between the first and second partition plates to allow one specimen container to pass therethrough.

* * * * *